(12) United States Patent  
van Lengerich

(10) Patent No.: US 6,723,358 B1
(45) Date of Patent: Apr. 20, 2004

(54) ENCAPSULATION OF COMPONENTS INTO EDIBLE PRODUCTS

(75) Inventor: Bernhard H. van Lengerich, Plymouth, MN (US)

(73) Assignee: General Mills, Inc., Minneapolis, MN (US)

( * ) Notice: Subject to any disclaimer, the term of this patent is extended or adjusted under 35 U.S.C. 154(b) by 0 days.

(21) Appl. No.: 09/673,983

(22) PCT Filed: Mar. 23, 1999

(86) PCT No.: PCT/US99/04267
§ 371 (c)(1),
(2), (4) Date: Feb. 1, 2001

(87) PCT Pub. No.: WO99/48372
PCT Pub. Date: Sep. 30, 1999

Related U.S. Application Data

(63) Continuation-in-part of application No. 09/233,443, filed on Jan. 20, 1999.
(60) Provisional application No. 60/109,696, filed on Nov. 24, 1998, provisional application No. 60/103,700, filed on Oct. 9, 1998, and provisional application No. 60/079,060, filed on Mar. 23, 1998.

(51) Int. Cl.[7] .............................................. A21D 13/00
(52) U.S. Cl. ............................. 426/94; 426/61; 426/89; 426/549; 424/439
(58) Field of Search .......................... 426/94, 61, 89, 426/549, 96, 285, 302; 424/439

(56) References Cited

U.S. PATENT DOCUMENTS

| | | |
|---|---|---|
| 2,876,160 A | 3/1959 | Schoch et al. |
| 3,027,102 A | 3/1962 | Lödige et al. |
| 3,404,984 A | 10/1968 | Olsen |
| 3,786,123 A | 1/1974 | Katzen |
| 3,868,471 A | 2/1975 | Decelles et al. |
| 3,922,354 A | 11/1975 | Galluzzi et al. |
| 3,928,567 A | 12/1975 | Andersen et al. |
| 3,962,416 A | 6/1976 | Katzen |
| 3,992,555 A | 11/1976 | Kovacs |
| 4,075,356 A | 2/1978 | Haag et al. |
| 4,106,991 A | 8/1978 | Markussen et al. |
| 4,178,392 A | 12/1979 | Gobble et al. |
| 4,242,219 A | 12/1980 | Bogerman et al. |
| 4,357,358 A | 11/1982 | Schanze |
| 4,379,171 A | 4/1983 | Furda et al. |
| 4,532,145 A | 7/1985 | Saleeb et al. |
| 4,689,235 A | 8/1987 | Barnes et al. |
| 4,816,259 A | 3/1989 | Matthews et al. |
| 4,820,534 A | 4/1989 | Pickup et al. |
| 4,871,574 A | 10/1989 | Yamazaki et al. |
| 4,886,820 A | 12/1989 | Gross et al. |
| 4,888,171 A | 12/1989 | Okonogi et al. |
| 4,895,725 A | 1/1990 | Kantor et al. |
| 4,999,208 A | 3/1991 | Lengerich et al. |
| 5,009,900 A | 4/1991 | Levine et al. |
| 5,023,083 A | 6/1991 | Drell |
| 5,071,668 A | 12/1991 | van Lengerich et al. |
| 5,074,902 A | 12/1991 | Connick, Jr. et al. |
| 5,075,058 A | 12/1991 | Chan et al. |
| 5,079,012 A | 1/1992 | Lengerich et al. |
| 5,087,461 A | 2/1992 | Levine et al. |
| 5,118,513 A | 6/1992 | Mehansho et al. |
| 5,183,690 A | 2/1993 | Carr et al. |
| 5,296,000 A | 3/1994 | Darmont et al. |

(List continued on next page.)

FOREIGN PATENT DOCUMENTS

| | | |
|---|---|---|
| DE | 37 38 042 A | 5/1988 |
| DE | 40 21 678 | 1/1992 |
| EP | 33662 A | 10/1969 |

(List continued on next page.)

OTHER PUBLICATIONS

Niness, "Breakfast Foods and the Health Benefits of Inulin and Oligofructose", *Cereal Foods World*, vol. 44, No. 2, Feb. 1999, pp. 79–81.

The Scots Kitchen, Abernethy biscuits recipe from the web site www.scotweb.com.uk/kitchen/BAK/abernethy.html, based upon "A Taste of Old Scotland" by Micheil Rob Mac Phadruig, last updated May 24, 1999.

Per Artusson et al., "Characterization of Polyacryl Starch Microparticles as Carriers for Proteins and Drugs," *Journal of Pharmaceutical Science*, vol. 73, No. 11, pps. 1507–1513 (Nov. 1984).

(List continued on next page.)

*Primary Examiner*—Lien Tran
(74) *Attorney, Agent, or Firm*—Douglas J. Taylor; Barry I. Hollander; John A. O'Toole

(57) ABSTRACT

An edible matrix composition that has a chewable texture and that contains at least one encapsulated component is obtained by admixing at least one plasticizer, and a ground, free-flowing particulate mixture which comprises at least one fat, at least one starch, and at least one sugar which have been mixed and heated without substanitially gelatinizing the starch. A chewable texture is obtained rather than a hard, glassy matrix because the starch is substantially ungelatinized. However, a flavorful product is obtained without destroying a heat sensitive encapsulant because the starch is admixed with ingredients comprising fat or oil and sugar and the mixture is heated to develop flavor at high temperatures prior to admixing with the heat sensitive encapsulant. The encapsulated component may be at least one biologically active component, pharmaceutical component, nutraceutical component, or microorganism. In preferred embodiments, the free-flowing mixture is obtained by grinding cookies. The free-flowing mixture, such as ground cookies and the plasticizer, such as oil and water are mixed with an encapsulant to obtain a formable dough or crumbly mass. The formable dough is shaped or formed into pieces or pellets and dried to a shelf-stable moisture content

67 Claims, No Drawings

U.S. PATENT DOCUMENTS

| | | |
|---|---|---|
| 5,320,669 A | 6/1994 | Lim et al. |
| 5,431,929 A | 7/1995 | Yatka et al. |
| 5,466,460 A | 11/1995 | McMahon et al. |
| 5,514,387 A | 5/1996 | Zimmerman et al. |
| 5,567,730 A | 10/1996 | Miyashita et al. |
| 5,597,416 A | 1/1997 | Fuisz et al. |
| 5,683,720 A | 11/1997 | Myers et al. |
| 5,744,180 A | 4/1998 | Cherukuri et al. |
| 5,750,104 A | 5/1998 | Sipos |
| 5,820,903 A | 10/1998 | Fleury et al. |
| 5,851,553 A | 12/1998 | Myers et al. |
| 5,894,029 A | 4/1999 | Brown et al. |
| 5,902,617 A | 5/1999 | Pabst |
| 5,939,127 A | 8/1999 | Abboud |
| 5,958,502 A | 9/1999 | Fulger et al. |
| 5,972,373 A | 10/1999 | Yajima et al. |
| 5,972,395 A | 10/1999 | Saleeb et al. |
| 5,972,404 A | 10/1999 | van Lengerich |
| 5,972,415 A | 10/1999 | Brassart et al. |
| 5,976,603 A | 11/1999 | Kota et al. |
| 6,004,594 A | 12/1999 | van Lengerich |
| 6,008,027 A | 12/1999 | Langner |
| 6,024,994 A | 2/2000 | Jacobson et al. |
| 6,048,551 A | 4/2000 | Amidon et al. |
| 6,149,965 A | 11/2000 | van Lengerich et al. |
| 6,168,811 B1 | 1/2001 | Clark et al. |
| 6,174,553 B1 | 1/2001 | Cerda et al. |
| 6,190,591 B1 | 2/2001 | van Lengerich |
| 6,242,033 B1 | 6/2001 | Sander |
| 6,261,613 B1 | 7/2001 | Narayanaswamy |
| 6,284,268 B1 | 9/2001 | Mishra et al. |
| 6,342,257 B1 | 1/2002 | Jacobson et al. |
| 6,368,621 B1 | 4/2002 | Engel et al. |
| 2001/0044026 A1 | 11/2001 | Vaghefi |

FOREIGN PATENT DOCUMENTS

| | | |
|---|---|---|
| EP | 0 223 963 A | 6/1987 |
| EP | 391518 A | 10/1990 |
| EP | 0 462 012 A2 | 12/1991 |
| EP | 0 465 364 A1 | 1/1992 |
| EP | 552057 A | 7/1993 |
| EP | 603992 A1 | 6/1994 |
| EP | 605913 A | 7/1994 |
| EP | 1 064 856 A2 | 1/2001 |
| EP | 1066 761 A2 | 1/2001 |
| EP | 1 118 274 A | 7/2001 |
| FR | 2 640 472 A | 6/1990 |
| GB | 15312 | of 1911 |
| GB | 1 437 501 A | 5/1976 |
| JP | 47014316 A | 10/1972 |
| JP | 59139317 A | 8/1984 |
| JP | 1313421 A | 12/1989 |
| JP | 6024962 A | 2/1994 |
| JP | 2000139372 A | 5/2000 |
| WO | WO 85/04074 | 9/1985 |
| WO | WO 88/01512 A | 3/1988 |
| WO | 91 03940 | 4/1991 |
| WO | WO 92/00130 | 1/1992 |
| WO | WO 92/00140 | 1/1992 |
| WO | WO 92/12645 | 8/1992 |
| WO | WO 94/23593 | 10/1994 |
| WO | WO 95/00121 | 1/1995 |
| WO | WO 95/18544 | 7/1995 |
| WO | WO 95/26752 | 10/1995 |
| WO | 96 09773 | 4/1996 |
| WO | 96 14058 | 5/1996 |
| WO | WO 97/16076 | 5/1997 |
| WO | WO 97/38016 A | 10/1997 |
| WO | WO 97/39116 | 10/1997 |
| WO | WO 98/02148 A | 1/1998 |
| WO | WO 98/09981 A | 3/1998 |
| WO | WO 98/18610 | 5/1998 |
| WO | WO 98/35704 A | 8/1998 |
| WO | WO 98/50019 A | 11/1998 |
| WO | WO 98/54980 | 12/1998 |
| WO | WO 98/58642 A | 12/1998 |
| WO | WO 99/11242 A1 | 3/1999 |
| WO | WO 99/20745 A1 | 4/1999 |
| WO | WO 99/23896 | 5/1999 |
| WO | WO 99/34688 | 7/1999 |
| WO | WO 99/45904 A1 | 9/1999 |
| WO | WO 99/48372 | 9/1999 |
| WO | WO 99/56563 | 11/1999 |
| WO | WO 99/61002 A1 | 12/1999 |
| WO | WO 99/65336 | 12/1999 |
| WO | WO 00/21504 | 4/2000 |
| WO | WO 00/41740 A2 | 7/2000 |
| WO | WO 00/64436 A1 | 11/2000 |

OTHER PUBLICATIONS

Lennart Randen et al., "Coprecipitation of Enzymes with Water Soluble Starch—An Alternative to Freeze–drying," *J. Pharm. Pharmacol.*, vol. 40, pps. 763–766 (1988).

Shigeaki Maruo et al., "Effects of Moranoline, 4–O–α–D–Glucopyranosylmoranoline and Their N–Substituted Derivatives on Thermostability of Cyclodextrin Glycosyltransferase, Glucoamylase, and β–Amylase," *Biosci. Biotech. Biochem.*, vol. 57, No. 8, pps. 1294–1298, (1993).

Wendell Q. Sun et al., "Protein stability in the amorphous carbohydrate matrix: relevance to anhydrobiosis," *Biochimica et Biophysica Acta*, vol. 1425, pps. 245–254 (1998).

Colonna et al., "Extrusion Cooking of Starch & Starchy Products," *Extrusion Cooking*, C. Mercier, et al. AACC, St. Paul, MN (1989), pps. 247–319.

Meuser et al., "A Systems Analytical Approach To Extrusion," *Food Extrusion Science & Technology*, ed. J. Kokini, Dekker Publ. (1992), pps. 619–630.

Brochure entitled "Innovate With Raftiline®," Orafti Active Food Ingredients, Nov. 1996.

"Inulin–A 'Good–for–you' Fat Replacer, Texture Modifier," *Food Formulating*, p. 15, Feb. 1997.

Brighenti, F., et al., "One Month Consumption of Ready-–to–eat Breakfast Cereal Containing Inulin Markedly Lowers Serum Lipids in Normolipidemic Men," from: Proceedings of the 7th FENS European Nutrition Conference, 1995.

Silva, R., "Use of Inulin as a Natural Texture Modifier," *Cereal Foods World*, Oct. 1996, vol. 41, No. 10, pps. 792–794.

Arshady R., "Microcapsules for Food," *Journal of Microencapsulation*, vol. 10, No. 4, pp. 413–435, Oct. 1, 1993, Taylor and Francis Inc., London, GB.

ENCAPSULATION OF COMPONENTS INTO EDIBLE PRODUCTS

This application is a 371 application of PCT/US99/04267 filed Mar. 23, 1999 and is a continuation in part of application Ser. No. 09/233,443 filed Jan. 20, 1999, and claims the benefit of provisional application Nos. 60/079,060 filed Mar. 23, 1998, No. 60/103,700 filed Oct. 9, 1998 and No. 60/109,696 filed Nov. 24, 1998.

FIELD OF THE INVENTION

The present invention relates to compositions, the use and the manufacturing of edible products, that contain encapsulated or embedded components, such as nutraceutical components, pharmaceuticals, biologically active components, and/or live microorganisms. The products according to this invention are intended to be consumed either directly as a food or they may be used as additions to food, such as topical applications or in beverages. They are not intended to undergo additional severe processing that might thermally or mechanically destroy the encapsulant. The products made according to this invention exhibit eating qualities, such as a chewable texture, as it occurs in for example streusel or chewable vitamin pills, and a cookie-like taste.

BACKGROUND OF THE INVENTION

Encapsulation of food components is described in *Encapsulation and Controlled Release of Food Ingredients*, edited by S. J. Risch and G. A. Reineccius, ACS Symposium Series 590 (1995). U.S. Pat. No. 5,183,690 to Carr, et. al. describes a continuous extrusion process using starch-based material to encapsulate components. The resulting products are in the form of particulates, which have gelatinized starch as a continuous domain, in which discontinuous domains of biologically active core material is entrapped.

Encapsulation of heat sensitive components, for example nutraceutical components, such as for example microorganisms, into matrixes that are edible, is generally difficult for a number of reasons. First, conventional encapsulation processes which expose matrix material and encapsulants to high temperatures, causes thermal destruction or loss of encapsulant. Thus, either large overdoses of encapsulant, which would be very expensive, would be required, or the encapsulant would not sustain the encapsulation process at all. Second, if the encapsulant can be encapsulated into a matrix under sufficiently low temperatures, the resulting product is a solid, that is characterized as substantially hard and glass-like. The hardness and glassiness is caused by cooking a starch-based material with a sufficient amount of water to gelatinize the starch and subsequently separating the starch-based materials into discrete particles and drying them so that the water content of the starchy mass is sufficiently low. However, the temperature at which the particles are consumed, or the eating temperature, is generally lower than 50° C., which is far below the glass transition temperature, $T_g$, of the cooked, dried starch. Therefore, products of this kind exhibit a dense and glassy, very hard texture, that may be very suitable to encapsulate components. However, when chewed they cause severe problems, because they are not chewable and exhibit a texture similar to that of uncooked rice or pasta. They can therefore be only swallowed as microtablets without chewing. They could also be used as dense pellets for a variety of processing applications, where a controlled release of the heat sensitive encapsulant is desired. The physical hardness of the products and their mechanical stability are advantageous for many processing applications. However, chewing or masticating of these products would be very unpleasant and their incorporation into other food products is not practical.

The present invention provides an edible product, that is chewable, has a pleasant taste and texture and contains encapsulated components, particularly nutraceutical, pharmaceutical or biologically active components. The chewable product can be used either as a food product itself, or as part of a food product, i.e. as an ingredient or as a topping, that may be applied to surfaces of food. A main physical characteristic of the product made according to the present invention is that the product is substantially less hard than foods products such as uncooked rice and raw pasta. The chewable, flavorful product can be eaten either alone as a food itself, or for example as medical food, as food having a pharmaceutical effect, as a dietary supplement, or in combination with other foods, such as a topping or in pasty foods or beverages.

SUMMARY OF THE INVENTION

The present invention provides a product that contains an encapsulated nutraceutical component, pharmaceutical component, biologically active component, or live microorganisms, or a combination thereof. In preferred embodiments, the product contains an encapsulated microorganism. The products of the present invention contain the one or more encapsulants in a pleasantly tasting and chewable surrounding matrix.

The matrix composition of the present invention comprises a plasticizer, such as oil and/or water, and a substantial amount of a free flowing mixture of at least one fat, one starch and one sugar, that are preprocessed, i.e. mixed and heat treated so as to substantially prevent gelatinization of starch and to provide a pleasantly tasting product. An example of the free flowing mixture is fine ground-up cookies having a particle size of 100% smaller than about 1 mm.

The mixture may contain additional components to enhance preprocessing or to improve sensory attributes, such as flavor, sodium chloride, nonfat dry milk, whey protein, high fructose corn syrup, dextrins, and leavening agents, as well as other components known to those skilled in the art of producing pleasantly tasting cookie type products.

The matrix may further comprise components that either facilitate processing, or mask the unpleasant taste of the encapsulants, or prevent exposure to oxygen or air, or which enhance the sensory attributes of the final product. These components include, for example, lipids, such as oils or fats, chocolate liquor, chocolate, cocoa powder, compound coatings, flavors, concentrated fruit juice, or particulates, such, as for example ground nuts or almonds. The water may be pH adjusted to obtain a good tasting product.

A chewable texture is obtained rather than a hard, glassy matrix because the starch is substantially ungelatinized. However, a flavorful product is obtained without destroying a heat sensitive encapsulant because the starch is admixed with ingredients comprising fat or oil and sugar and the mixture is heated to develop flavor at high temperatures prior to admixing with the heat sensitive encapsulant.

In accordance with the method of the present invention, a product containing a substantial amount of a free-flowing material in which the starch component is substantially ungelatinized may be obtained by grinding a baked product, such as cookies or cookie-type products, to obtain a free-flowing particulate mixture or flour. The reduced particle size facilitates the formation of a dough or crumbly mass upon mixing of the free-flowing mixture with a plasticizer such as water and/or oil. In embodiments of the invention, the particle size of a cookie-type product or cookies may be reduced to obtain a dry, free-flowing particulate mixture having a particle size of about 100% smaller that 1 mm.

Admixing of the free-flowing mixture, such as ground-up cookie flour, with at least one plasticizer such as water and/or oil and the encapsulant with the other components to obtain a dough or crumbly mass may be performed continuously using an extruder or continuous mixer. The dough or crumbly mass may be formed or pressed into discrete particles. Moisture may be removed from the particles to an amount sufficiently low so as to obtain a sufficient shelf life. The products made according to the invention exhibit a granular, crumbly structure having a pleasant taste and are chewable.

DETAILED DESCRIPTION OF THE INVENTION

An edible, starch-based matrix composition that contains at least one encapsulated component and that is chewable, rather than hard and glassy is obtained from a ground pre-processed, free-flowing particulate mixture and at least one plasticizer without substantially gelatinizing the starch. The free-flowing mixture may be obtained by admixing and heating at least one fat, at least one starch, and at least one sugar without substantially gelatinizing the starch. The encapsulated component may be one or more biologically active components, pharmaceutical components, nutraceutical components, microorganisms, or mixtures thereof. In embodiments of the invention, the free-flowing mixture may be obtained by baking a mixture of said at least one fat, at least one starch, and at least one sugar without substantially gelatinizing said at least one starch to obtain a baked product and then grinding the baked product to obtain the free-flowing mixture. In preferred embodiments, the free-flowing mixture is at least substantially ground cookies or a flour obtained by grinding cookies.

A key requirement of the free-flowing mixture, such as ground-up cookie flour or ground-up cracker flour is that its starch component, which may originate from grain sources such as wheat, oats, barley, corn, rye, or other grains or potatoes or other roots, is substantially not gelatinized. Production of a free-flowing mixture without substantially gelatinizing starch can be accomplished in known manner by any one ordinarily skilled in the art of making cookies or cookie-type products. If the free-flowing mixture contained substantial amounts of gelatinized starches, the process would result in products that after drying exhibit substantial glassiness, hardness and thus a mechanical stability that is undesirable. The substantially gelatinized, glassy, hard products would not exhibit desirable sensory attributes.

If the matrix composition was made from a pasta flour, such as for example semolina, the mechanical characteristics of the final product would be similar to commonly known uncooked pasta and would be undesirably hard for direct consumption. Products made from soft wheat flour that has not been cooked or processed into a cookie-type product, would exhibit inferior taste and would be undesirable for direct consumption.

A cookie-type product for use in the present invention may be made by known conventional cookie production processes. As is well known, cookie production comprises admixing of at least fat and sugar, and adding flour to the premixed sugar/fat mix to obtain a cookie dough. Optionally, minor ingredients and water can be added to facilitate machining of the dough, and to obtain a typical texture and taste of the final cookie. The cookie dough is formed into individual pieces and baked under conventional baking conditions. The baking is generally performed above the gelatinization temperature of starch, but the starch is not substantially gelatinized because sufficient amounts of water are not accessible to the starch at the elevated temperatures. However, the baking helps to develop flavor, through Maillard reactions for example, and develops a leavened, crumb structure.

Conventional or commercially available cookie or other baked good formulations and ingredients may be used to produce the free-flowing mixtures employed in the present invention. Examples of cookies and cookie-like products which may be ground for use in the present invention are butter cookies, sugar cookies, graham crackers, chocolate chip cookies, oatmeal cookies, sugar wafers, almond cookies, chocolate cookies, vanilla wafers, mixtures thereof, and the like.

Exemplary amounts of ingredients which may be used to obtain a free-flowing mixture are: from about 10% by weight to about 40% by weight fat, from about 20% by weight to about 40% by weight sugar, and from about 45% by weight to about 75% by weight flour, preferably wheat flour, based upon the total weight of the fat, sugar and flour in the free-flowing mixture.

Conventional minor and other conventional cookie ingredients, which may be included in the free-flowing mixture, such as ground cookies, are for example, high fructose corn syrup, maltodextrins, corn syrup, dextrose, maltose, modified or unmodified starches, eggs, leavening agents such as sodium bicarbonate, ammonium bicarbonate baking soda, and calcium phosphate, non-fat dry milk, full-fat dry milk, whey proteins, gluten, natural or artificial flavors, insoluble and soluble fibers, such as inulin, hydrocolloids, such as guar gum or gum arabic, dry eggs, salt, nutrients, and emulsifiers such as mono- and diglycerides.

In embodiments of the invention, ground cookies employed as a free-flowing mixture in the present invention may comprise from about 8% by weight to about 40% by weight shortening or fat, from about 15% by weight to about 40% by weight sugar, and from about 20% by weight to about 75% by weight flour, based upon the weight of the ground cookies.

In embodiments of the invention, after baking and cooling, a cookie product or a commercially available cookie may be ground up into a flour or powder or meal using a conventional mill or other grinding apparatus. The particle size distribution may preferably be similar to that of a flour. The ground flour has a preferred particle size of 100% smaller than 1 mm to form a continuous dough phase. In embodiments of the invention, the ground, particulate free-flowing mixture may have a particle size distribution of 100% less than 10 mm. However, with a much coarser particle size, (for example if the majority of the particles were 5 mm) the ground product would not yield a uniform dough and would produce a granular, nonhomogeneous phase. Much finer powders, for example 100% less than 50 micron would create processing difficulties, such as feeding problems, dusting, and caking to processing surfaces. In preferred embodiments at least a substantial portion of the ground, free-flowing particulate mixture has a particle size distribution of from about 50 microns to about 1 mm.

Another requirement of the free-flowing mixture such as ground cookies is that its starch component is substantially ungelatinized. This may be accomplished, during the process of cookie making for example, by mixing and/or coating the starch-containing components with fat before adding optional moisture. Another possibility is to entrap added moisture in fat and prevent moisture access to the starch in the flour. At least substantially ungelatinized starch in the final ground cookie or other free-flowing mixture tends to resist subsequent gelatinization when mixed with water. In embodiments of the invention the starch in the free-flowing mixture, such as ground cookies, and in the matrix compositions of the present invention has a degree of starch gelatinization of less than about 50%, preferably less than about 30%, preferably less than about 15%, as measured by differential scanning calorimetry (DSC).

The free-flowing mixture, such as ground cookies is used in an effective encapsulating amount. In embodiments of the present invention, the free-flowing mixture content, such as the cookie or cracker flour content of the particles may be at least about 10% by weight, generally at least about 30% by weight, for example from about 60% by weight to about 95% by weight, based upon the weight of the edible, chewable matrix composition. The amount of free-flowing mixture, such as ground cookies employed may depend upon the desired texture and the plasticizer employed. For example, if water is employed as the plasticizer, generally the free-flowing mixture content of the chewable matrix composition is higher, for example, at least about 40% by weight, because water is removed during drying to obtain a shelf stable product. If the plasticizer employed does not have to be removed to obtain a shelf-stable product, the free-flowing mixture content may be lower. For example, if the plasticizer is a fat which is at least substantially solid at room temperature, the free-flowing mixture content may be at least about 10% by weight, based upon the weight of the edible, chewable matrix composition.

Plasticizers employed in the present invention may be any edible or consumable liquid which enables the formation of a substantially homogeneous cohesive, plasticized, viscoelastic, formable mixture, dough or crumbly mass. Exemplary of plasticizers which may be used are water, an aqueous-based composition such as a sugar solution, juice, alcohol, glycerol, and sorbitol, oils, melted shortenings or fat, and mixtures thereof.

The amount of liquid plasticizer, such as water and/or oil, should generally be sufficient to obtain a formable mixture or dough at a sufficiently low temperature and under sufficiently low shear conditions so as to avoid substantial mechanical or thermal destruction of the free-flowing mixture or encapsulant. Exemplary total amounts of plasticizer, such as oil and/or water, used to form a dough or crumbly mass may range up to about 90% by weight, generally from about 10% by weight to about 70% by weight, for example from about 20% by weight to about 45% by weight, based upon the total weight of the free-flowing mixture, such as ground cookies, and the added plasticizer used to form the dough or crumbly mass.

If water is employed as a plasticizer, it may generally be used in an amount of less than or equal to about 25% by weight, based upon the total weight of the free-flowing mixture and added water to obtain a formable, extrudable dough. Higher amounts are less desirable, because more drying may be needed to obtain a shelf-stable product. When an edible oil, shortening or fat is employed as a plasticizer, it may generally be used in an amount of up to about 90% by weight, preferably up to about 20% by weight, most preferably up to about 10% by weight, based upon the total weight of the free-flowing mixture, such as ground cookies and the oil, shortening or fat.

Generally, higher amounts of the encapsulant component may be encapsulated in the matrix composition when an oil, shortening or fat is used as a plasticizer because generally higher amounts of oil may be employed compared to the amount of water which may be employed. Use of an oil or fat as a plasticizer in place of or in addition to water is advantageous because the oil or fat in addition to facilitating extrusion, also serves as a preencapsulation medium. The oil or fat provides a protective coating on the free-flowing mixture, such as ground cookies, and on the encapsulant. Also, the need for drying of the dough to obtain a shelf-stable moisture content is substantially reduced or eliminated when oil or fat is employed as a plasticizer. The addition of vegetable oil during mixing has been proven useful to obtain a smooth continuous dough phase and it facilitates forming of the dough into discrete particles.

Edible oils, shortenings or and fats which may be employed include those derived from plant, animal, and marine sources such as vegetable shortening or oils, which include corn oil, safflower oil, soybean oil, and cotton seed oil, which may be hydrogenated, as well as edible fat substitutes. In embodiments of the invention, particularly where high levels of oil or fat are employed, the melting point of the oil, shortening or fat should be sufficiently high so as to avoid separation of oil during extrusion. For example, the melting point of the oil, shortening or fat may be at least about 30° C., preferably at least about 37° C., most preferably at least about 40° C.

In embodiments of the invention, the formable mixture or dough may have a total plasticizer content, such as water and/or oil, of up to about 90% by weight, generally from about 10% by weight to about 50% by weight, for example about 15% by weight to about 25% by weight. The total plasticizer content may include water supplied by any liquid encapsulant component and additional plasticizer, such as added water, glycerol, sorbitol or a combination thereof or any other liquids, such as fruit juice, that enables the formation of a dough. When water or low melting point oils are employed at high levels, for example a moisture content well above 50%, a thin, low viscosity dough may result. The low viscosity dough may either not be formable or the drying efforts would be unnecessarily high. Substantially lower moisture contents, such as well below 5% may result in a dry product, which would be too fragile after forming and would fall apart. It may also generate frictional heat during extrusion forming which would be detrimental to the heat sensitive encapsulant. The water may be mixed with organic acids or fruit juice to adjust pH and to obtain a pleasant flavor in the final product.

In embodiments of the invention, where for example, removal of plasticizer is not needed to obtain a shelf-stable matrix composition, the plasticizer content of the edible, chewable matrix composition may be at least substantially the same as the plasticizer content of the formable mixture, dough or crumbly mass. For example, in embodiments of the invention when an oil, shortening or fat is employed as a plasticizer, the plasticizer content of the edible, chewable matrix composition may be up to about 90% by weight, for example from about 10% by weight to about 50% by weight, based upon the weight of the matrix composition.

The liquid plasticizer content of any liquid encapsulant component utilized may be at least about 35% by weight, generally at least about 50% by weight, for example from about 65% by weight to about 90% by weight, based upon the weight of the liquid encapsulant component.

For example, an aqueous dispersion of *Lactobacillus acidophilus* may have a moisture content of about 70% by weight and an encapsulant content (*Lactobacillus acidophilus*) of about 30% by weight. The 70% moisture content stemming from the acidophilus dispersion may be used as a plasticizer. The ratio of the free-flowing mixture to moisture stemming from the aqueous encapsulant liquid may be about 3:1 to enable the formation of a homogeneous dough. Vegetable oil may be added to delay penetration of water into the matrix and delay the release of the microorganism. The encapsulation of sensitive liquid components into a matrix to obtain discrete shelf-stable particles is disclosed in U.S. patent application Ser. No. 09/233,443 filed Jan. 20, 1999 in the name of Bernhard H. van Lengerich for "Encapsulation of Sensitive Liquid Components into a Matrix to Obtain Discrete Shelf-stable Particles," the disclosure of which is herein incorporated by reference in its entirety.

Edible, plasticizable matrix components which form a glassy matrix, such as gelatinized starches, and other ingredients may be included in the chewable, matrix compositions of the present invention provided they do not adversely affect the chewable texture of the matrix composition. Gelatinized starches may, for example, be included in an amount up to about 30% by weight of the free-flowing mixture, such as ground cookies.

Examples of optional, edible, plasticizable matrix materials which are plasticizable at low temperatures by the plasticizer component may be a plasticizable biopolymer such as a carbohydrate, such as a starch or cyclodextrin, polyethylene glycol, pentosans, hydrocolloids such as carragenan, alginates, or gum arabic, wheat gluten, such as vital wheat gluten or isolated gluten, and mixtures thereof. Exemplary starches which may be used are native or modified starches or pregelatinized starches derived from corn, wheat, rice, potato, tapioca, or high amylose starch. Sources of starch which may be used also include flours from grains such as corn, wheat, durum wheat, rice, barley, oat, or rye, and mixtures thereof. In preferred embodiments, finely ground or powdered cookies or crackers, or ground cookie-like or cracker-like products are employed with substantially no additional, plasticizable, gelatinized matrix materials.

Additional matrix components which may be used include solid components which are substantially non-plasticizable at temperatures lower than the decomposition temperature of the heat sensitive encapsulant. Exemplary of such optional, substantially non-plasticizable matrix components are at least substantially non-gelatinized starch, carbohydrates which have a lower molecular weight than starches, fiber, or other inert materials, such as cellulose, or hemi-cellulose. The lower molecular weight matrix components tend to dissolve more readily than does starch and increase the penetrability or porosity of the matrix. As a result, access by the dissolution medium, such as water or acid, to the encapsulant is increased thereby permitting quicker release of the encapsulant from the matrix material. Examples of carbohydrates other than starch which may be used are sugars, such as mono- and di-saccharides, and starch hydrolyzate products such as dextrins or syrups with dextrose equivalent values (DE values) ranging from about 2 to about 99, or from about 5 to 98, and mixtures thereof Additional ingredients which may be used to control the release properties of the final product may be a hydrophobic agent for slowing down the rate of release of the encapsulant. Exemplary of components which may be added to affect the hydrophobicity of the matrix composition include fats, oils, waxes, fatty acids, emulsifiers, such as mono- or di-glycerides, modified starches from plant sources that possess hydrophobic properties that are obtained via either physical or chemical modification, and mixtures of hydrophobic components. Plant lipids or synthetic lipids with melting points up to about 65° C. may, for example, be employed as a hydrophobic agent. The hydrophobic components increase the hydrophobicity of the matrix and help to prevent or delay penetration of water or gastric juice into the matrix by repelling water or aqueous acids, thereby delaying the release of the encapsulant into the surrounding media.

Additional components which may be used to delay or prevent a fast release of the encapsulant from the matrix are components or agents which have a high water binding capacity. The agents may have a water binding capacity or water holding capacity which is greater than the water binding capacity of the free-flowing mixture, such as ground cookies. The high water binding capacity component may bind water which penetrates the particles, or prevent the water from dissolving the matrix, thereby preventing or delaying the release of the encapsulant from the matrix. Exemplary of high water binding capacity agents which may be used in the present invention are protein from animal sources such as gelatin, casein, and protein from sources such as wheat, soy, corn, or other grains, and hydrocolloids such as carrageenans, alginates, xanthan gum, gum arabic, guar flour or guar gum, agar, tragacanth, karaya, locust bean gum, pectin, soluble fiber, insoluble fiber and the like. Exemplary proteins from grains which may be used are gluten, vital wheat gluten, zein, and soy protein concentrate. The proteins from plant sources may also be used to increase the tolerable addition of lipids within the matrix composition and thereby indirectly increase the hydrophobicity of the matrix. The high water binding capacity components may be used alone or mixtures thereof may be employed.

Process compatible additional components to facilitate processing, or to improve sensory attributes such as the taste, texture, aroma, color, appearance, or hydration behavior of the final pellets which may be employed include: flavors, sodium chloride, nonfat dry milk, whey protein, high fructose corn syrup, leavening agents, lipids, such as oils or fats, chocolate liquor, chocolate, cocoa powder, compound coatings, concentrated fruit Juice, or particulates, such as ground nuts or almonds. The water may be pH adjusted to obtain a good tasting product. The addition of vegetable oil during mixing has been found useful to obtain a smooth continuous dough phase and it facilitates forming of the dough and cutting into discrete particles without sticking.

The additional components or ingredients, such as those used to control the rate of release of the encapsulant may be used in amounts up to about 70% by weight, preferably from about 5% by weight to about 50% by weight, most preferably from about 10% by weight to about 35% by weight, based upon the weight of the free-flowing mixture, such as ground-up cookies.

The encapsulant may be in solid or liquid form for inclusion in the matrix compositions and encapsulated products of the present invention. Active components which may be encapsulated or embedded in the matrixes in accordance with the present invention include pharmaceutical compositions or compounds, nutraceutical compositions or compounds, nutritional components, or biologically active components, flavorants, and fragrances.

The pharmaceutical compounds or compositions and biologically active compositions may, for example, include antibiotics, analgesics, vaccines, antiinflammatory agents, antidepressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, and steroids, compositions to promote growth such as hormones, or other growth stimulating agents, mixtures thereof, and the like.

Nutraceutical components may include components which promote health or prevent disease or enhance well-being such as antioxidants, phytochemicals, hormones, vitamins such as Vitamins A, B1, B2, B6, B12, C, D, E, K, pantothenate, folic acid, pro-vitamins, minerals such as calcium, selenium, magnesium salts, available iron, and iron salts, microorganisms such as bacteria, such as live lactobacilli, fungi, and yeast, prebiotics, probiotics, trace elements, essential and/or highly unsaturated fatty acids such as omega-3 fatty acids, and mid-chain triglycerides, nutritional supplements, enzymes such as amylases, proteases, lipases, pectinases, cellulases, hemicellulases, pentosanases, and phytases, pigments, oligopeptides, dipeptides, and amino acids, and mixtures thereof.

Exemplary of the active components which may be encapsulated or embedded in accordance with the present invention are: acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amdinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethasone diproionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine and aspirin and codeine, beta-carotene, calcifediol, calcium carbonate, calcium citrate, calcium salts, candicidin, captopril, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozil, ceftazidime, cefuroxime axetil, cephalexin, cephradine, chlorambucil, chloramphenicol, chlordiazepoxide, chloroquine phosphate, chlormadinone acetate, chlorothiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clinda-mycin hydrochloride, -palmitate and -phosphate, clioquinol, clofazimine, clofibrate, clomriphene citrate, clonazepam, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cyclophosphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, dichlorphenamide, dicloxacillin sodium, dicyclomine, dienestrol, diethylpropion hydrochlorid, diethylstilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfiram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalapril maleate, analaprilat, ephedrine, epinephrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopropazine hydrochloride, ethotoin, ethynodiol diacetate, etidronate disodium, etoposide, eugenol, famotidine, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ibuprofen, ifosfamide, imipramide, imipramide hydrochloride, indapamide, indomethacin, insulin, inulin, iocetamid, iodoquinol, iohexol, iopamidol, ipecac, ipodate calcium, ipodate sodium, isocarboxacid, isoetharine hydrochloride, isoflurane, isoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocarnithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, lonetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measle virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenytoin, mephobarbital, meprednisone, meprobamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, naloxone, nandrolone decanoate, nandrolone phenpropionate, naproxen, natamycin, neomycin, neomycin sulfate, neostimine bromide, niacin, nitrofurantoin, nalidixic acid, nifedipine, nitrazepam, nitrofurantoin, nitroglycerine, nitromerson, nizatidine, nonoxynol 9, norethindrone, norethindrone acetate, norfloxacin, norgestrel, nortriptyline hydrochloride, noscapine, novobiocin sodium, nystatin, opium, oxacillin sodium, oxamniquine, oxandrolone, oxazepam, oxprenolol hydrochloride, oxtriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin b sulfate, polythiazide, potassium chloride, potassium citrate, potassium cluconate, potassium iodine, potassium sodium tartrate, povidone iodine, pralidoxime chloride, pramoxine hydrochloride, pramezam, prazepam, praziquantel, prazosin hydrochloride, prazosin hydrochloride, prednisolone, prilocaine, primaquine, primidone, probenecid, probucol, procainamide hydrochiorid, procaine hydrochloride, procarbacine hydrochloride, prochlorperazine, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamnine, pyroxylin, pyrvinium pamoate, phenacetin, phenytoin, prednisone, uinidine gluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salicylic acid, salsalata, scopolamine, secobarbital sodium, selenius acid, selenium sulfate, sennasenrne, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine, thioridazine hydrochloride, thistrepton, thiotepa, thiothixene, threonine, thyroid, ticarcillin, timolol, tioconazole, titaniumdioxide, tolazamide, tolbutamide, tolmetin, tolnaftate, trazodone hydrochloride, tretinoin, triacetin, triamcinolone, triamterene, triazolam, trichorfon, trichlormethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, trisulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefiine, silymarin, dihydroergotamine, buflomedil, etofibrate, indometacin, urea, valine, valproic acid, vancomycin hydrochloride, vasopressin, verapramil, vidarabine, vinblastine, vincristine, vitamins, warfarin, yellow fever vaccine, zinc acetate, zinc carbonate, zinc chloride, zinc gluconate, beta acetyl digoxin, piroxicam, haloperidol, ISMN, amitriptylin, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)rutoside, propicillin, aciclovir mononitrate, paracetamol, naftidrofuryl, pentoxiflline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetam, phenoxymethylpenicillin, furosemide, bromazepam, flunarizin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, pnimidone, clobazam, oxaceprol, medroxyprogesterone, flecainid, pyridoxal 5 phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metilsulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

The amount of the active component or encapsulant which is incorporated into the products of the present invention may be such so as to provide or deliver an effective amount, such as a pharmaceutically effective amount or a nutraceutically effective amount of the active component at its intended location, such as the small intestine. Exemplary amounts of the active component or encapsulant which may be encapsulated or embedded into the matrix may be from about 1% by weight to about 85% by weight, preferably from about 3% by weight to about 50% by weight, most preferably from about 5% by weight to about 30% by weight, based upon the weight of the free-flowing mixture, such as ground cookies. In embodiments of the invention, the amount of the active component or encapsulant may be up to about 80% by weight, preferably up to about 50% by weight, most preferably up to about 20% by weight of the plasticizer, such as oil.

In embodiments of the invention, the encapsulants and/or the edible, chewable matrix composition may be coated to provide additional protection against oxygen, to provide mechanical stability against abrasion, or to control release of the encapsulant without negatively influencing the chewable texture of the matrix composition. Film-building or film-forming substances which may be used to coat encapsulants prior to admixing with the free-flowing mixture and prior to incorporation into the matrix include commonly used coating materials. Exemplary of coating materials which may be employed are zein, pectin, shellac, gelatin, gluten, fats, oils, waxes, emulsifiers, native or modified starch, chitosan, chitin, and mixtures thereof These film-building or film-forming substances may also be used to coat the extruded, particulate chewable product. Pretreatment of the encapsulant by coating it with a film forming substance such as a high melting fat or wax, or with an emulsifier such as glycerin monostearate, or the like, tends to prevent unwanted interaction between an encapsulant and the matrix. The encapsulants and the extrudate particles may be coated with film-forming amounts of the substances in aqueous or alcoholic solutions, or oleaginous compositions. The encapsulants may be pre-encapsulated or pre-coated using any conventional encapsulation or coating method which does not thermally destroy the encapsulant.

In embodiments of the invention pellets may be coated in a two step coating process. After discrete particles have been cut at an extrusion die, the substantially undried pellets may be coated with a first component of a composite coat, such as an acetic-acid-chitosan-solution. After this step a second coat may be applied using a gel forming counter ion, such as a polyphosphate solution, that causes the chitosan to gel and form a chitin coat. The second ion may also be provided by a pectin and the resulting composite coat may then be a pectin-chitin coacervate.

The film-forming substances or coatings may also contain additional components that protect the particulates or pellets, or encapsulant, from the influence of light, such as titanium dioxide, or cocoa-based products. The coatings may also contain anti-oxidants to protect the pellets or encapsulants from the influence of oxygen or air.

In accordance with embodiments of the present invention, the thickness of the coating upon the encapsulant may be used to control the rate of release of encapsulant once the dissolving media, such as water, reaches the encapsulant. For example, increasing the thickness of the coating on the encapsulant slows its rate of release into the media. Also, increasing the thickness of the coating on the extrudate or pellet delays release of the encapsulant from the matrix material. In embodiments of the invention, the amount of coating may range from about 0.5% to about 50% by weight, based on weight of the total product, depending upon the desired release of the encapsulant.

In accordance with the method of the present invention, all of the ingredients may be admixed together at a temperature of about 5° C. to about 50° C., for example about 30° C. to obtain a formable mixture or dough. Mixing or dough temperatures substantially higher than about 50° C. are undesirable, because any fat or oil in the formula tends to separate, or the heat sensitive substances to be encapsulated and embedded would be destroyed. Temperatures much lower than room temperatures, such as for example 0° C. are for most purposes impractical but may be employed in special applications. In embodiments of the invention, the temperature may be adjusted by external heating, below 50° C. so as to facilitate forming and enable cutting without the material sticking to the cutter.

In embodiments of the present invention, external heating of the ingredients during their admixture is not required. For example, where ground cookies is used as the free-flowing matrix material, heating of the ground cookies and water to cook or gelatinize the starch is not needed to obtain a formable dough which when dried to a shelf-stable moisture content provides a chewable texture.

The admixing of the ingredients is conducted under low shear mixing conditions without substantially destroying or decomposing the matrix material or encapsulant. An overall quantitative measure of the shear used inside an extruder, for example, is the specific mechanical energy input. In embodiments of the present invention, the specific mechanical input during admixing of the ingredients to obtain a formable mixture or dough may be below about 150 Wh/kg, preferably below about 100 Wh/kg, and most preferably below about 50 Wh/kg.

In embodiments of the invention, the pressure under which the formable mixture or dough may be formed may range from about 1 bar to about 100 bars. It is preferably formed into individual shapes at pressures of about 5 bars to about 60 bars.

The optional one or more additional ingredient or component, such as the hydrophobic component, or high water binding capacity component for controlling the release properties of the final product, may be dry blended or preblended with the free-flowing matrix material such as ground cookies. In other embodiments of the invention, the additional component for controlling the release properties may be added separately.

The encapsulant may be added either during the dough mixing process or it may be added into the dough after it is produced. After addition and admixing of the encapsulant, the dough may be compressed and shaped into discrete shapes.

In embodiments of the invention, a dough comprising all ingredients may be made using conventional batch or continuous mixers. Subsequently, the dough, which may be a crumbly dough may be fed into a single screw extruder. The single screw extruder presses the dough against a die plate and plasticizes the crumbs into a continuous dough phase which may then be pressed through an extrusion die and subsequently cut into individual particulates.

In other embodiments of the invention, the dough can be made continuously and using a continuous mixer or extruder alone. Twin screw extruders or co-rotating twin screw mixers may be advantageously used which enable the steps of continuously mixing the dough and subsequently extruding the dough through an extrusion die plate. Co-rotating intermeshing twin screw extruders, such as those available from Buhler, Switzerland, Clextral France, Werner and Pfleiderer Germany, APV England or Wenger USA, or a Co-Kneader, available from Buss, Switzerland may be employed.

For feeding solid components to an extruder, conventional solids feeding devices such as a volumetric or gravimetric feeder may be used. Liquid injection nozzles may be used for injecting liquid active components or solutions, dispersions, emulsions or suspensions. In embodiments of the invention, a side feeder and liquid injection nozzles may be employed. If an injection nozzle is used, the pressure for injecting the liquid encapsulant should be sufficiently higher than the pressure in the extruder so that the encapsulant can be injected into the extruder barrel. For example, if the pressure of the plasticized mass inside the extruder is 10 bars, the injection pressure may be about 2 to about 5 bars higher, i.e. 12 to 15 bars.

In embodiments where an encapsulant is pre-coated with a film-building material or coating material, the coating material may be applied in conventional manner such as by spraying or enrobing using conventional coating equipment. Commercially available pre-coated active ingredients, such as precoated minerals or vitamins may be employed.

The admixing of the added active ingredients or encapsulants inside the extruder may be accomplished by using an appropriate extrusion screw configuration for achieving low shear mixing. For example, a combination of alternating small pitch conveying elements with distributive mixing elements, that are staggered at an angle to each other for providing axially oriented leakage flow inside the extruder barrel may be employed. The combination of alternating conveying elements with distributive mixing elements cause the material flow to be continuously interrupted without shearing of the mass thus resulting in mixing of the material at low mechanical energy input.

In other embodiments of the invention, other extruder screw configurations may be used that facilitate low shear distributive mixing, such as screw elements of the type ZME, TME, SME, and so-called IGEL elements commercially available from Werner and Pfleiderer.

The total length of the distributive mixing section may be about 3 to 12 l/d, preferably about 4 to 6 l/d to sufficiently admix and distribute and embed or encapsulate the added active components in the matrix.

The at least substantially homogeneous mixture of matrix material and added active ingredient or encapsulant may then be conveyed towards an extruder die plate. The conveying may be achieved by the use of low pitch extruder screw conveying elements which build up sufficient pressure prior to extruding the mix so that it can be forced through the apertures in the die plate. Another function of the low pitch elements is that they increase the degree of fill inside the last extruder barrel section. The increased degree of fill enables control of the temperature profile of the mix inside the extruder barrel for achieving optimum viscosity adjustment and extrusion through the subsequent die openings.

The dough or crumbly mass or mix may be extruded or pressed through extrusion dies having aperture diameters of from about 0.3 mm to about 5 mm, preferably from about 0.5 mm to about 3 mm, for example from about 0.5 mm to about 1 mm. The diameter of the extrudate rope and product may be larger than the diameter of the die apertures due to deformation or swelling as the composition exits the die. The increase in diameter upon exiting the die may occur without substantial development of an expanded, puffed, foamy, or cellular structure. The extruded rope may have a cross-sectional diameter of from about 0.5 mm to about 7 mm, preferably from about 0.5 mm to about 5 mm, most preferably from about 0.5 mm to about 3 mm.

The extrudate rope may be cut at the die face using a rotating cutter, pelletizer, or rotating knives. In other embodiments, the extrudate rope may be cut away from the die using conventional cutting or forming means for producing pellets or tablets. The cut pieces, pellets, or tablets, may have a length:diameter ratio (l/d ratio) of about 0.5 to 10, preferably about 1.

In accordance with the process of the present invention, the particle size may be varied to control the surface to volume ratio of the pellets or pieces for achieving a desired controlled release of the encapsulant. The particle size may be varied, for example, by the use of different diameters for the extrusion die openings. Particle size may also be varied by the use of a variable speed cutter either at the die plate at the end of the extruder or away from the extruder after the ropes have been conveyed for a short distance. By varying the speed of the cutter, the size of the cut pieces may be varied for a given extruder throughput. The use of a variable cutter which is spaced a short distance from the die plate, for example, between about 0.5 meters to about 5 meters permits further surface cooling, further surface drying, and reduced stickiness to provide better cutting of the ropes into pellets.

In producing products for human or animal consumption, variation of particle size to control the surface to volume ratio of the pellets is critical for achieving a controlled release of the encapsulant during passage of the pellets or particles through the mouth, the stomach, and the intestine. Variation of particle size is also critical for controlling the residence time of the pellets inside the stomach. For example, particles smaller than 1 mm pass through the stomach or intestine faster than would particles larger than for example 2.5 mm.

After cutting, the resulting pieces or pellets may be dried to a sufficiently low moisture content which assures a sufficiently prolonged storage stability or shelf life. For example, the pellets may be dried to achieve a storage stability or shelf life of at least about six months, preferably at least about twelve months, most preferably at least about thirty-six months. In embodiments of the present invention, the drying may be performed using conventional drying equipment using drying temperatures which do not adversely affect the thermal stability of the encapsulants. Exemplary drying temperatures may range from about 10° C. to about 50° C., for example about 30° C. The drying may be conducted to achieve a moisture content of less than about 30% by weight, preferably less than about 12% by weight, most preferably less than about 10% by weight, for example less than about 8% by weight.

The product may be dried using a conventional fluidized bed or other conventional drying means. The product may be optionally coated after drying using conventional coating equipment such as coating pans, coating drums, or spray devices.

In embodiments where film-building substances or coatings are applied to the particles or pellets, conventional spray nozzles may be located close to the die for spraying an aqueous or alcoholic solution of the film-building substances onto the cut pieces as they fall downwardly from the extruder die. In other embodiments, the film-building substances may be applied after drying of the pellets. For example, the film-building substances may be applied using spray nozzles, conventionally known fluid bed coating apparatus, or other conventional coating apparatus and methods. If the application of the film-building substances increases the moisture content above a shelf stable level, the water or other volatile media may be removed from the surface of the particles by additional drying.

In embodiments of the present invention, the extruded pieces or pellets may be compressed in conventional tablet presses to obtain compressed versions of the extruded pellets.

In other embodiments of the present invention, the mixture may be extruded or formed into bars or into a rope which may be cut into food bar-sized pieces. The mixture may also be extruded through a sheeting die into a sheet. The extruded sheet may then be cut or molded into individual pieces, such as bars, snack-sized pieces, tablets, or disks, using a rotary die or rotary cutter, or reciprocating cutter or counterrotating drums conventionally known as agglomeration drums or tableting drums.

The products of the present invention may possess a chewable texture, like that of streusel or chewable vitamin pills with a cookie-like taste. They may comprise food bar or snack-sized pieces, or they may comprise discrete particles which may be spherical, lens-shaped, or flat discs having diameters of from about 0.5 mm to about 7 mm, preferably from about 0.5 mm to about 5 mm, most preferably from about 1 mm to about 3 mm, exclusive of any optional exterior film-building substances or coatings. In embodiments of the invention, the particles of the invention may be in the form of tablets with diameters of up to about 10 mm. The length-to-diameter ratio (l/d) of the particles may be from about 0.1 to about 10, for example about 0.5 to about 2, preferably about 1. The particles are generally uniform in size, non-glassy, and granular to increase palatability to humans and animals in a substantially compact form that is easy to swallow with or without chewing. The products of the invention are non-expanded, generally not leavenable, and exhibit a non-puffed, substantially non-cellular, non-glassy structure. The starch component of the matrices may be substantially ungelatinized, and not substantially destructurized or dextrinized. Exemplary specific densities of the products of the present invention are between about 800 g/liter and about 1500 g/liter (about 0.8 to about 1.5 g/cm$^3$).

The encapsulated products of the present invention may be incorporated with or without grinding into foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain snacks, and microwave popcorn, dairy products such as yoghurt, cheese, and ice cream, sweet goods such as hard candy, soft candy, and chocolate, beverages, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food preblends or mixes for home or food service use, such as preblends for soups or gravy, dessert mixes, dinner mixes, baking mixes such as bread mixes, and cake mixes, and baking flour.

In preferred embodiments, the active encapsulant is either a live microorganism, enzyme, micronutrient, trace element, nutraceutical component, biologically active material or a combination thereof The encapsulated product may be redispersed as a liquid, or as a solid for human food, animal feed, or pharmaceutical purposes. The products of the present invention may be used as or incorporated into foods for special purposes, such as performance foods, mood foods, medical foods, nutritional snacks or supplements, sport foods such as power bars, baby foods, toddler foods, infant foods, or foods for pharmaceutical purposes or other dietetic purposes. The discrete particulates or granules of the present invention may be used as a topping for breakfast cereals, snacks, soups, salad, cakes, cookies, crackers, puddings, desserts or ice cream. They may also be used as a granular ingredient for yogurts, desserts, puddings, custards, ice cream or other pasty or creamy foods. Regularly sized pieces may be individually packaged or used as nutritional snacks or, for example added to or formed into nutritional food in bar form.

The present invention is further illustrated by the following non-limiting examples where all parts, percentages, proportions, and ratios are by weight, and all temperatures are in ° C. unless otherwise indicated:

EXAMPLE 1

Production of Good Tasting and Chewable Pellets Having Encapsulated Live Microorganism In this example 10 kg cookies (Leibnitz Keks, Bahlsen, Germany) were ground with a hammer mill into a flour having a particle size of 100% less than 1 mm. This flour was fed at a rate of 4 kg/h into a twin screw extruder (Werner & Pfleiderer, ZSK22). A mix of water and citrus juice (ratio 7:1) was fed at a rate of 0.8 kg/h into the same extruder. 0.188 kg of *Lactobacillus Acidophilus* was preblended with 0.375 kg vegetable fat (BISKIN) and 0.188 kg vegetable oil and the preblend was fed at a rate of 0.750 kg/h into a subsequent barrel of the same extruder. The barrel temperature of the extruder was kept at 20° C. The extruder conditions were:

| | |
|---|---|
| rpm | 150 revolutions per minute |
| Pressure | 45 bar |

-continued

| Product Temperature | 31° C. |
| Die | 20 × 1 mm diameter |

The product was cut into individual pellets at the die face with a rotating knife. The pellets were dried at 30° C. in a convection batch dryer for 1 hr to 5.9% moisture. The pellets containing live Lactobacilli exhibit a pleasant taste and chewable texture.

EXAMPLE 2
Coating With Thin Additional Coat

A portion of the pellets made in Example 1 were coated with a 25% shellac/alcohol solution to obtain a 5% shellac coat based on the total weight of the total product. These pellets containing live lactobacilli exhibit a pleasant taste and chewable texture, that was slightly harder than the uncoated sample, but still chewable and eatable.

EXAMPLE 3
Coating With Thick Additional Coat

Another portion of the pellets obtained in Example 1 were coated with a 25% shellac/alcohol solution to obtain a 10% shellac coat based on the total weight of the total product. The obtained pellets containing live lactobacilli exhibit a pleasant taste and chewable texture, that was slightly harder than the 5% coated sample of Example 2, but they were still chewable and eatable.

COMPARATIVE EXAMPLE

Semolina flour was fed at a rate of 4 kg/h into a twin screw extruder (Werner & Pfleiderer, ZSK22). Water was fed at a rate of 1.5 kg/h into the same extruder. 0.18 kg of *Lactobacillus Acidophilus* was preblended with 0.36 kg vegetable fat (BISKIN) and 0.18 kg vegetable oil and the preblend was fed at a rate of 0.72 kg/h into a subsequent barrel of the same extruder. The barrel temperature of the extruder was kept at 20° C.

The extruder conditions were:

| rpm | 120 revolutions per minute |
| Pressure | 20 bar |
| Product Temperature | 29° C. |
| Die | 20 × 1 mm diameter |

The product was cut into individual pellets at the die face with a rotating knife. The pellets were dried at 30° C. in a convection batch dryer for 1 hour to 8.25% moisture.
The pellets containing live lactobacilli exhibit a very hard and unacceptable texture to be eaten as such. The texture was comparable to that of uncooked pasta.

What is claimed is:

1. An edible matrix composition that has a chewable texture and that contains at least one component encapsulated by the matrix composition, said matrix composition comprising at least one plasticizer, and a free-flowing particulate mixture which comprises at least one fat, at least one starch, and at least one sugar which have been mixed and heated, said at least one starch having a degree of gelatinization of less than about 50%.

2. An edible matrix composition as claimed in claim 1 wherein said free-flowing mixture is obtained by baking a mixture of said at least one fat, at least one starch, and at least one sugar without substantially gelatinizing said at least one starch to obtain a baked product and then grinding the baked product to obtain said free-flowing mixture.

3. An edible matrix composition as claimed in claim 1 wherein said free-flowing mixture is ground cookies.

4. An edible matrix composition as claimed in claim 1 wherein said plasticizer comprises a fat or oil.

5. An edible matrix composition as claimed in claim 1 wherein said plasticizer comprises water.

6. An edible matrix composition as claimed in claim 1 wherein the free-flowing mixture content is at least about 10% by weight, based upon the weight of said edible matrix composition.

7. An edible matrix composition as claimed in claim 4 wherein the plasticizer content is from about 10% by weight to about 70% by weight, based upon the total weight of said free-flowing mixture and said plasticizer.

8. An edible matrix composition as claimed in claim 1 wherein the plasticizer content is up to about 90% weight, based upon the weight of said edible matrix composition.

9. An edible matrix composition as claimed in claim 1 wherein the plasticizer comprises oil or fat, and the oil or fat plasticizer content is up to 90% by weight, based upon the weight of said edible matrix composition.

10. An edible matrix composition as claimed in claim 9 wherein the melting point of said oil or fat plasticizer is at least about 30° C.

11. An edible matrix composition as claimed in claim 5 wherein the moisture content of the edible matrix composition is less than about 8% by weight, based upon the weight of the matrix composition.

12. An edible matrix composition as claimed in claim 1 wherein said at least one component is selected from the group consisting of biologically active components, pharmaceutical components, nutraceutical components and microorganisms.

13. An edible, chewable matrix composition as claimed in claim 1 wherein the starch content of the matrix composition consists essentially of the starch content of said free-flowing mixture.

14. An edible matrix composition as claimed in claim 3 wherein said ground cookies comprise from about 8% by weight to about 40% by weight shortening or fat, from about 15% by weight to about 40% by weight sugar, and from about 20% by weight to about 75% by weight flour, based upon the weight of the ground cookies.

15. An edible matrix composition as claimed in claim 1 wherein said at least one component comprises live probiotic microorganisms.

16. An edible matrix composition as claimed in claim 15 wherein said at least one component comprises live lactobacilli.

17. An edible matrix composition as claimed in claim 12 which is coated with a coating composition in an amount of from about 0.5% by weight to about 50% by weight, based upon the weight of the coated product.

18. An edible chewable matrix composition as claimed in claim 1 further including at least one flavor or texture enhancing ingredient selected from the group consisting of chocolate, flavors, concentrated juices, fibers, and compound coatings.

19. An edible matrix composition as claimed in claim 18 wherein said at least one flavor or texture enhancing ingredient is selected from the group consisting of emulsifiers, oils and fats.

20. An edible matrix composition according to claim 3 wherein said ground cookies contain at least one component selected from the group consisting of high fructose corn syrup, maltodextrins, corn syrup, dextrose, lactose, maltose, modified or unmodified starches, leavening agents, non-fat dry milk, full fat dry milk, whey, gluten, soluble and insoluble fiber, nutrients, inulin, hydrocolloids, dry eggs, salt, flavor, emulsifier, cocoa, and cocoa butter.

21. An edible and chewable product comprising:
    a) a free-flowing particulate mixture which comprises at least one fat, at least one starch, and at least one sugar which have been mixed and heated, said at least one starch having a degree of gelatinization of less than about 50%, and
    b) an encapsulant,
        wherein the encapsulant is embedded or encapsulated in a dough made substantially from the free-flowing mixture and a plasticizer, said dough being dried to a shelf-stable moisture content.

22. An edible and chewable product as claimed in claim 21 wherein said free-flowing mixture comprises a flour obtained by grinding cookies.

23. An edible and chewable product as claimed in claim 21 wherein said encapsulant comprises at least one member selected from the group consisting of biologically active components, neutraceutical components, and live microorganisms.

24. An edible and chewable product as claimed in claim 21 wherein said encapsulant is pre-encapsulated.

25. An edible and chewable product as claimed in claim 21 wherein said encapsulant is heat sensitive.

26. An edible and chewable product as claimed in claim 21 wherein said encapsulant has an undesirable taste which is masked by said free-flowing mixture.

27. An edible and chewable product as claimed in claim 21 which is coated with a coating composition.

28. An edible and chewable product as claimed in claim 21 which is a food bar.

29. An edible and chewable product as claimed in claim 21 which is in granular form.

30. A food composition comprising an edible and chewable product as claimed in claim 21 which is selected from the group consisting of ready-to-eat breakfast cereals, snacks, soups, salads, cakes, cookies, crackers, puddings, ice creams, yogurts, puddings, custards, baby foods, medicinal foods, sports bars, and beverages.

31. A food composition as claimed in claim 30 which is a yogurt, pudding, custard, or ice cream wherein said edible and chewable product is in granular form.

32. A food composition as claimed in claim 30 which is a breakfast cereal, snack, soup, salad, cake, cookie, cracker, yogurt, pudding, custard, or ice cream wherein said edible and chewable product is applied as a topping.

33. A food composition as claimed in claim 30 which is a beverage.

34. A food composition comprising a topping which is an edible and chewable product as claimed in claim 30.

35. A food topping comprising an edible matrix composition as claimed in claim 1 in granular form.

36. An edible, chewable matrix composition comprising:
    a liquid plasticizer,
    an encapsulant, and
    a flour comprising ground cookies,
        wherein the starch content of the matrix composition has a degree of gelatinization of less than about 50% so as to provide a chewable, non-glassy texture to the matrix composition, and
        wherein the encapsulant is encapsulated by plasticized ground cookies.

37. An edible, chewable matrix composition as claimed in claim 36 wherein said encapsulant comprises at least one member selected from the group consisting of biologically active components, pharmaceutical components, neutraceutical components and microorganisms.

38. An edible, chewable matrix composition as claimed in claim 36 wherein the amount of said ground cookies is at least about 10% by weight of said chewable matrix composition.

39. An edible, chewable matrix composition as claimed in claim 36 wherein the moisture content of the chewable matrix composition is less than about 8% by weight, based upon the weight of the matrix composition.

40. An edible, chewable matrix composition as claimed in claim 36 which is in particulate form.

41. An edible, chewable matrix composition as claimed in claim 36 wherein the starch content of the matrix composition consists essentially of the starch content of said ground cookies.

42. A method for the manufacture of edible products containing an encapsulated component comprising:
    a) mixing a free-flowing particulate mixture with a plasticizer to obtain a crumbly mass or dough, said free-flowing mixture comprising a flour made from at least one fat, at least one starch, and at least one sugar which have been mixed and heated so that said at least one starch has a degree of gelatinization of less than about 50%,
    b) admixing at least one encapsulant into the crumbly mass or dough,
    c) compressing the crumbly mass or dough to obtain a compressed dough,
    d) shaping the compressed dough, and
    e) separating the shaped dough into individual pieces,
        wherein ingredients comprising the free-flowing mixture, plasticizer, and encapsulant are admixed, compressed and shaped at temperatures sufficiently low so as to prevent thermal degradation of the encapsulant and at pressures sufficiently high to enable the formation of coherent pieces.

43. A method as claimed in claim 42 wherein at least said mixing is performed in a continuous mixer or in a twin screw extruder.

44. A method as claimed in claim 42 wherein the compressed dough is shaped by extrusion.

45. A method as claimed in claim 42 wherein said free-flowing mixture is obtained by baking a mixture of said at least one fat, at least one starch, and at least one sugar without substantially gelatinizing said at least one starch to obtain a baked product and then grinding the baked product to obtain said free-flowing mixture.

46. A method as claimed in claim 42 wherein said free-flowing mixture is ground cookies.

47. A method as claimed in claim 42 wherein said plasticizer comprises at least one member selected from the group consisting of fats, oils, and water.

48. A edible matrix composition as claimed in claim 42 wherein said plasticizer comprises fat or oil.

49. A method as claimed in claim 42 wherein said free-flowing mixture comprises a flour obtained by grinding cookies to a particle size of less than about 5 mm.

50. An edible matrix composition as claimed in claim 1, wherein said at least one component comprises a pharmaceutical composition, a nutraceutical composition, a flavorant, or a fragrance.

51. An edible matrix composition having a chewable texture comprising:

a matrix comprising at least one plasticizer and a free-flowing particulate mixture, said free-flowing mixture comprising at least one fat, at least one starch, and at least one sugar which have been mixed and heated without substantially gelatinizing said at least one starch; and at least one component encapsulated by the matrix and selected from the group consisting of analgesics, anti-inflammatory agents, anti-depressants, anti-viral agents, anti-tumor agents, enzyme inhibitors, steroids, hormones, HIV protease inhibitors, and mixtures thereof.

52. An edible matrix composition having a chewable texture comprising:

a matrix comprising at least one plasticizer and a free-flowing particulate mixture, said free-flowing mixture comprising at least one fat, at least one starch, and at least one sugar which have been mixed and heated without substantially gelatinizing said at least one starch; and at least one component encapsulated by the matrix and selected from the group consisting of antioxidants, phytochemicals, vitamins, folic acid, pantothenate, minerals, fatty acids, enzymes, amino acids, and mixtures thereof.

53. An edible matrix composition having a chewable texture comprising:

a matrix comprising at least one plasticizer and a free-flowing particulate mixture, said free-flowing mixture comprising at least one fat, at least one starch, and at least one sugar which have been mixed and heated without substantially gelatinizing said at least one starch; and an omega-3 fatty acid encapsulated by the matrix.

54. An edible matrix composition according to claim 1, wherein said at least one starch has a degree of gelatinization of less than about 30%.

55. An edible matrix composition according to claim 1, wherein said at least one starch has a degree of gelatinization of less than about 15%.

56. An edible matrix composition according to claim 1, wherein said at least one plasticizer is selected from the group consisting of a sugar solution, juice, alcohol, glycerol, and sorbitol.

57. An edible matrix composition according to claim 1, wherein said at least one plasticizer is an alcohol.

58. An edible and chewable product according to claim 21, wherein said at least one starch has a degree of gelatinization of less than about 30%.

59. An edible and chewable product according to claim 21, wherein said at least one starch has a degree of gelatinization of less than about 15%.

60. An edible, chewable matrix composition according to claim 36, wherein the starch content of the matrix composition has a degree of gelatinization of less than about 30%.

61. An edible, chewable matrix composition according to claim 36, wherein the starch content of the matrix composition has a degree of gelatinization of less than about 15%.

62. A method according to claim 42, wherein said free-flowing mixture comprises a flour made from at least one fat, at least one starch, and at least one sugar which have been mixed and heated so that said at least one starch has a degree of gelatinization of less than about 30%.

63. A method according to claim 42, wherein said free-flowing mixture comprises a flour made from at least one fat, at least one starch, and at least one sugar which have been mixed and heated so that said at least one starch has a degree of gelatinization of less than about 15%.

64. An edible matrix composition according to claim 51, wherein said at least one starch has a degree of gelatinization of less than about 50%.

65. An edible and chewable product according to claim 52, wherein said at least one starch has a degree of gelatinization of less than about 50%.

66. An edible and chewable product according to claim 53, wherein said at least one starch has a degree of gelatinization of less than about 50%.

67. An edible matrix composition that has a chewable texture, comprising:

a matrix comprising at least one plasticizer, and a free-flowing particulate mixture which comprises at least one fat, at least one starch, and at least one sugar which have been mixed and heated, said at least one starch having a degree of gelatinization of less than about 30%; and

*lactobacillus* encapsulated by the matrix.

\* \* \* \* \*